United States Patent [19]

Panster et al.

[11] Patent Number: 4,507,490

[45] Date of Patent: Mar. 26, 1985

[54] PROCESS FOR THE PRODUCTION OF SULFUR CONTAINING ORGANOSILICON COMPOUNDS

[75] Inventors: Peter Panster, Rodenbach; Rudolf Michel, Freigericht; Peter Kleinschmit; Ulrich Deschler, both of Hanau, all of Fed. Rep. of Germany

[73] Assignee: Degussa Aktiengesellschaft, Frankfurt am Main, Fed. Rep. of Germany

[21] Appl. No.: 593,308

[22] Filed: Mar. 26, 1984

[30] Foreign Application Priority Data

Mar. 29, 1983 [DE] Fed. Rep. of Germany ....... 3311340

[51] Int. Cl.$^3$ ............................. C07F 7/08; C07F 7/18
[52] U.S. Cl. .................................................... 556/427
[58] Field of Search ........................................ 556/427

[56]  References Cited

U.S. PATENT DOCUMENTS

| 3,284,466 | 11/1966 | Rosenthal | 556/427 X |
| 3,530,160 | 9/1970 | Gardner et al. | 556/427 |
| 3,842,111 | 10/1974 | Meyer-Simon | 556/427 |
| 3,873,489 | 3/1975 | Thurn et al. | 556/427 X |
| 3,997,581 | 12/1976 | Pletka | 556/427 |
| 4,072,701 | 2/1978 | Pletka | 556/427 |
| 4,129,585 | 12/1978 | Buder | 556/427 |
| 4,384,132 | 5/1983 | Schwarz et al. | 556/427 |

FOREIGN PATENT DOCUMENTS

| 2141159 | 3/1973 | Fed. Rep. of Germany | 556/427 |
| 2141160 | 3/1973 | Fed. Rep. of Germany | 556/427 |
| 2405758 | 8/1975 | Fed. Rep. of Germany | 556/427 |
| 2712866 | 11/1978 | Fed. Rep. of Germany | 556/427 |
| 2542534 | 11/1978 | Fed. Rep. of Germany | 556/427 |

OTHER PUBLICATIONS

Fieser et al., Organische Chemie, (1965), pp. 334–335.
Handbuch der Praparatwen Anorganischem Chemie, (1954), pp. 277–287.

Primary Examiner—Paul F. Shaver
Attorney, Agent, or Firm—Cushman, Darby & Cushman

[57] ABSTRACT

The invention is directed to a process for the production of sulfur containing organosilicon compounds by reaction of an oligosulfide obtained in the reaction solution from a hydrogen sulfide an alkali metal and sulfur with a haloalkylsilane.

7 Claims, No Drawings

PROCESS FOR THE PRODUCTION OF SULFUR CONTAINING ORGANOSILICON COMPOUNDS

BACKGROUND OF THE INVENTION

The invention is directed to a process for the production of sulfur containing organosilicon compounds.

In German Pat. No. 2,141,159 (and related Meyer-Simon U.S. Pat. No. 3,842,111, the entire disclosure of which is hereby incorporated by reference and relied upon), there is described a process for the production of bis(alkoxysilylalkyl)oligosulfides from the corresponding alkoxysilylhalides and alkali metal oligosulfides, preferably in alcoholic solution. Because of the easy hydrolyzability of the alkoxysilyl group this reaction always must be carried out under nearly water-free conditions.

The carrying out of the process is also made more difficult since on the one hand no water-free alkali metal oligosulfides are available and hence they first must be dehydrated by an expensive procedure which is likewise difficult because of its ready hydrolyzability and on the other hand, the production of water-free oligosulfides is associated with the development of unpleasant by-products, e.g. especially hydrogen sulfide.

Analogously this also is true for the process described in German Pat. No. 2,141,160 for the production of bis-(alkoxysilylalkyl)oligosulfides which provides for a reaction of alkoxysilylalkyl-mercaptans with sulfur dihalides or for a process described in German Pat. No. 2,405,758 (and related Pletka U.S. Pat. No. 3,997,581, the entire disclosure of which is hereby incorporated by reference and relied upon) which likewise starts from alkoxysilylalkyl-mercaptans and sulfur, or for a process described in German Pat. No. 2,542,534 (or related Pletka U.S. Pat. No. 4,072,701, the entire disclosure of which is hereby incorporated by reference and relied upon) which starts out from alkoxysilylalkyl-halides, metal or ammonium hydrogen sulfides and sulfur.

According to a process described in German Pat. No. 2,712,866 (and related Buder U.S. Pat. No. 4,129,585, the entire disclosure of which is hereby incorporated by reference and relied upon), there is reacted an alkali metal alcoholate with an alkoxysilylorganylhalide, metal or ammonium hydrogen sulfide and sulfur in the presence of an organic solvent.

However, the production of an alkali metal alcoholate solution requires such a large amount of time that apparently an industrial realization of the process is improbable.

The object of the invention is to develop a process for the production of sulfur containing organosilicon compounds which avoids the development of hydrogen sulfide, and which simultaneously makes possible a time saving production of oligo- and monosulfidic compounds.

SUMMARY OF THE INVENTION

The subject matter of the invention is a process for the production of sulfur containing organosilicon compounds of the formula $$Z-Alk-S_x-Alk-Z \qquad (1)$$

in which Z is the group

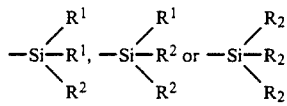

wherein
$R^1$ is a linear or branched alkyl group having 1-5 carbon atoms, a cycloalkyl group having 5-8 carbon atoms, a benzyl group, a phenyl group, or a phenyl group substituted by methyl, ethyl, or chloro,
$R^2$ is an alkoxy group with a linear or branched carbon chain having 1-5 carbon atoms or a cycloalkoxy group having 5-8 carbon atoms, the phenoxy group, or the benzyloxy group, and
wherein $R^1$ and $R^2$ in each case can have the same or different meaning,
Alk is a divalent saturated linear or branched hydrocarbon group having 1-10 carbon atoms, and
x is a number from 1.0 to 6.0 which comprises partially or completely dissolving in an organic solvent a hydrogen sulfide of the formula $$MeSH \qquad (2)$$

wherein Me is an alkali metal or an equivalent of an alkaline earth metal or of zinc or ammonium, then treating this dispersion or solution with an alkali metal after the end of the development of $H_2$, if x is $>1$, with the necessary amount of sulfur and directly subsequently further reacting with a compound of the formula $$Z-Alk-Hal \qquad (3)$$

wherein Z and Alk are as defined above and Hal is a chlorine or bromine atom, separating the organic product from the halide formed and removing the organic solvent.

The starting materials of formula (3) can be produced according to known processes and are generally available.

As alkali metal there is preferably used potassium or sodium even if Me of formula (2) has a different meaning.

As organic solvent in principle there can be employed all polar materials in which the hydrogen sulfide of formula (2) is at least partially soluble, and which neither reacts with the alkali metal nor with the organic silicon compound of formula (3) to form an undesired by-product. Alcoholotes, which may possibly be formed when employing alcohols do not effect the process of the invention.

Preferably there is employed as organic solvent a linear or branched alcohol having 1-5 carbon atoms such as e.g., methyl, ethyl, propyl, butyl or pentyl alcohol, as well as isopropyl alcohol, sec.butyl alcohol. Also suitable are cycloalkyl alcohols having 5-8 carbon atoms, e.g. cyclopentyl alcohol, cyclohexyl alcohol, cyclooctyl alcohol, phenyl or benzyl alcohol. It is useful in order to, e.g. avoid a transesterification, to employ the alcohol which in each case orresponds to the group $R^2$. In a given case, advantageously there can also be used a mixture of these alcohols, e.g. when $R^2$ has different meanings in a compound.

In carrying out the process of the invention as the compounds of formula (2) there are preferably used sodium, potassium, calcium, or ammonium hydrogen sulfides.

To carry out the reaction of the invention there is advantageously employed the elemental sulfur in finely divided form, for example, as commercial sulfur powder. Also the hydrogen sulfide is preferably employed in powder form to accelerate the reaction.

In the formulae (1) and (3) Alk signifies methylene as well as preferably ethylene, i-propylene, n-propylene, i-butylene, or n-butylene but can also be n-pentylene, 2-methylbutylene, 3-methylbutylene, 1,3-dimethylpropylene, n-hexylene, or n-decylene.

Illustrative compounds within formula (3) are 3-chloropropyltriethoxysilane, 3-bromopropyltriethoxysilane, chloromethyltrimethoxysilane, 2-chloroethyldiethoxyethylsilane, 2-bromoethyltri-i-propoxysilane, 2-chloroethyltriethoxysilane, 3-chloropropyltrimethoxysilane, 3-chloropropyldiethoxymethylsilane, 3-chloropropylcyclohexoxydimethylsilane, 4-bromobutyl-diethoxybenzylsilane, chlorobutyltrimethoxysilane, 5-chloropentyldimethoxyphenylsilane, 3-bromo-i-butyltriethyoxysilane, 3-chloropropyl-dimethoxy-p-ethylphenylsilane, 3-chloropropylethoxymethylethylsilane, 5-n-pentyldiethoxycyclo-pentylsilane, 3-bromopropyldimethoxycyclo-pentoxysilane, 2-chloro-2'-methylethyldiethoxycycloheptoxysilane, 3-bromo-2'-methylpropyldimethoxycylooctylsilane, 3-chloropropyldiethoxy-2'-methoxy-ethoxy-silane, 3-chloroethyldimethylcyclooctysilane, 3-chloropropyldibutozymethylsilane, 3-bromopropylphenyloxydimethoxysilane, 3-chloropropyldi-i-butozy-2'-methylphenysilane, 3-chloro-3'-methyl-propyldimethoxybenzyloxysilane, 3-chloropropyltributoxysilane, 3-chloropropyldiethoxyamysilane, and 3-chloropropyldiethoxy-p-methylphenylsilane.

There can be made as products any of the products within formula (1) mentioned for example in the above-mentioned Meyer-Simon U.S. patent, the Pletka U.S. patents and the Buder U.S. patent.

The reaction between the hydrogen sulfide and the alkali metal already begins spontaneously at room temperature and proceeds quantitatively within the shortest time and with heating of the solution. Suitably to reduce the total reaction time the procedure is carried out at elevated temperature or at a temperature increased to the boiling point of the solvent used, insofar as this is not disadvantageous to the quality of the product or effects the safety of the control of the reaction.

Furthermore it is recommended to carry out the reaction while excluding air and water (moisture) in order to suppress the formation of byproducts or to substantially avoid them. In the phase of development of hydrogen the operation can be under dry protective gas. It can also be suitable to carry out the reaction under reduced pressure; slightly elevated pressure likewise is not excluded.

In contrast to a portion of the precedingly described syntheses for bis(alkoxysilyalkyl)oligosulfides in this procedure of the invention there is no formation of hydrogen sulfide.

In contrast to the process described in German Pat. No. 2,712,866 (and the related Buder U.S. patent) it is emphasized that the process of the invention is carried out with a considerably reduced expenditure of time and even monosulfidic compounds can be produced.

The entire reaction starting, e.g. from sodium hydrogen sulfide and sodium, can be described through the equation

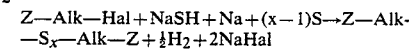

whereby x is 1.0–6.0.

The molar ratio of the reactants also is given in the preceding equation. After the complete combination in the described sequence it is advantageous to employ a post reaction time while the mixture is stirred under reflux. After the end of the reaction, the reaction mixture is cooled, the salt deposited separated off and then the organic solvent removed by distillation, whereby suitably there is employed reduced pressure. The sulfur containing organosilicon compounds formed as end products with the exception of the monosulfide derivatives under ordinary conditions cannot be distilled without decomposition. They are normally collected in the distillation sump and in most cases can be supplied wihou purification directly to the desired use. They can be employed as adhesive promoters or reinforcing additives in silicate fillers containing rubber mixtures.

Unless otherwise indicated, all parts and percentages are by weight.

The process can comprise, consist essentially of, or consist of the stated steps with the materials recited.

DETAILED DESCRIPTION

EXAMPLES

The general procedure is fully described in Example 1, additional examples of synthesized sulfur containing organosilicon compounds of formula (1) prepared using the process of the invention together with the amounts employed, the starting materials used, and the analytical data of the product are set forth in tabular form.

EXAMPLE 1

There were present in a 10 liter four neck flask equipped with a KPG stirrer, inner thermometer, reflux condenser, solid respectively liquid dosing apparatus a $N_2$ gassing apparatus and a waste gas line while simultaneously supplying nitrogen, 4.25 liters of ethanol and then 310 grams (5.25 moles) of about 95% sodium hydrogen sulfide. There were added to the milky solution 115 grams (5.0 moles) of sodium in the form of a piece. This dissolved within 30 minutes with the vigorous development of hydrogen and an increase in temperature up to reflux temperature. To the solution cooled to about 30° C. there were then added all at once, 481 grams (15.0 moles) of sulfur and directly subsequent there was begun the dosing of, in all, 2408 grams, (10.0 moles) of chloropropyltriethoxysilane, whereby the temperature in the sump again increased to reflux temperature. After about 50 minutes the silane component was completely added and then the mixture was stirred for a further 1.5 hours under reflux, then cooled, filtered over a Seitz pressure filter and the salt remaining on the filter washed twice with 200 ml of ethanol. After the ethanol was removed from the filtrate on the rotary evaporator at about 100 mbar pressure and up to a tempeature of 120° C., there remained as a light yellow clear liquid the desired product bis(3-triethoxysilylpropyl)-tetrasulfide in an amount of 2.66 kg (98.7% of theory).

The expected structure can be confirmed by NMR and IR spectroscopy. The index of refraction $n_D^{21}$ was determined to be 1.4938.

The analytical data read:

|  | % S | % C | % H | % Si |
|---|---|---|---|---|
| Found | 23.79 | 40.12 | 7.86 | 10.42 |
| Theory | 23.40 | 38.80 | 8.15 | 10.28 |

Following examples 2-9 were carried out analogously to Example 1. Insofar as it is a matter of a monosulfide derivative after the reaction of the sodium naturally there is carried out no further addition of sulfur but there is immediately begun the dosing of the haloorganylalkysilane to the cooled sulfide solution. Table 1 contains the most important date of Examples 2-9.

The entire disclosure of German priority application No. P 3311340.8 is hereby incorporated by reference.

$$Z-Alk-S_x-Alk-Z \qquad (1)$$

in which Z is the group

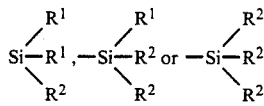

wherein

R$^1$ is an alkyl group having 1-5 carbon atoms, a cycloalkyl group having 5-8 carbon atoms, a benzyl group, a phenyl group, or a phenyl group substituted by methyl, ethyl, or chloro,

TABLE 1

| Example Nr. | Solvent (1) | Hydrogen Sulfide (g) | Sulfur (g) | Alkali Metal (g) | Silane (g) |
|---|---|---|---|---|---|
| 2 | C$_2$H$_5$OH 4,1 | NaSH (95%) 333 | — | Na 125 | Cl(CH$_2$)$_3$Si(OC$_2$H$_5$)$_3$ 2720 |
| 3 | C$_2$H$_5$OH 4,1 | NaSH (95%) 333 | — | Na 125 | Cl(CH$_2$)$_8$Si(OC$_2$H$_5$)$_3$ 3505 |
| 4 | C$_2$H$_5$OH 4,1 | NaSH (95%) 311 | 166,8 | Na 115 | Cl(CH$_2$)$_3$Si(OC$_2$H$_5$)$_3$ 2536 |
| 5 | CH$_3$OH 4,1 | NaSH (95%) 310 | 321 | Na 115 | Cl(CH$_2$)$_3$Si(OC$_2$H$_3$)$_3$ 1990 |
| 6 | CH$_3$OH 4,1 | KSH (94%) 384 | 481 | K 196 | Cl(CH$_2$)$_2$Si(OCH$_3$)$_3$ 1707 |
| 7 | i-C$_3$H$_7$OH 4,1 | NaSH (95%) 310 | 160,3 | Na 115 | Br(CH$_2$)$_3$Si(OC$_3$H$_7$)(C$_2$H$_5$)$_2$ 2673 |
| 8 | C$_2$H$_5$OH 4,1 | NaSH (95%) 310 | 321 | Na 115 | Cl(CH$_2$)$_5$Si(OC$_2$H$_5$)$_2$(C$_6$H$_5$) 3010 |
| 9 | C$_2$H$_5$OH 4,1 | NaSH (95%) 310 | 481 | Na 115 | Cl—CH$_2$—⟨○⟩—CH$_2$Si(OC$_2$H$_5$)$_3$ 3028 |

| Example Nr. | Formula (g) | % S Theor. Found | % C Theor. Found | % H Theor. Found | % Si Theor. Found |
|---|---|---|---|---|---|
| 2 | [(C$_2$H$_5$O)$_3$Si(CH$_2$)$_3$]$_2$S 2463 | 7.24 / 7.10 | 48.83 / 48.02 | 9.56 / 9.87 | 12.69 / 12.02 |
| 3 | [(C$_2$H$_5$O)$_3$Si(CH$_2$)$_8$]$_2$S 3159 | 5.50 / 5.32 | 57.68 / 56.90 | 10.72 / 10.93 | 9.63 / 9.27 |
| 4 | [(C$_2$H$_5$O)$_3$Si(CH$_2$)$_3$]$_2$S$_2$ 2401 | 13.50 / 13.43 | 45.53 / 44.86 | 8.92 / 9.22 | 11.83 / 11.29 |
| 5 | [(H$_3$CO)$_3$Si(CH$_2$)$_3$]$_2$S$_3$ 2082 | 22.75 / 21.29 | 34.10 / 33.46 | 7.15 / 7.10 | 13.29 / 12.74 |
| 6 | [(H$_3$CO)$_3$Si(CH$_2$)$_2$]$_2$S$_4$ 2120 | 30.05 / 29.06 | 28.15 / 27.20 | 6.14 / 6.38 | 13.16 / 13.85 |
| 7 | [(H$_5$C$_2$)$_2$(H$_7$C$_3$O) Si(CH$_2$)$_3$]$_2$S$_2$ 2175 | 14.61 / 14.09 | 54.74 / 53.71 | 10.57 / 10.42 | 12.80 / 12.17 |
| 8 | [(H$_5$C$_6$)(H$_5$C$_2$O)$_2$Si(CH$_2$)$_5$]$_2$S$_3$ 3100 | 15.34 / 14.76 | 57.46 / 57.00 | 8.04 / 8.22 | 8.96 / 8.51 |
| 9 | [(H$_5$C$_2$O)$_3$SiCH$_2$—⟨○⟩—CH$_2$]$_2$S$_4$ 3290 | 19.34 / 18.71 | 50.72 / 49.22 | 6.99 / 6.86 | 8.47 / 8.10 |

What is claimed is:

1. A process for the production of a sulfur containing organosilicon compound of the formula R$^2$ is an alkoxy group with a carbon chain having 1-5 carbon atoms or a cycloalkoxy group having 5-8 carbon, the phenoxy group, or the benzyloxy group,

Alk is a divalent saturated hydrocarbon group having 1–10 carbon atoms, and x is a number from 1.0 to 6.0 which comprises at least partially dissolving in a polar organic solvent, a hydrogen sulfide of the formula $$\text{MeSH} \quad (2)$$

wherein Me is an alkali metal or an equivalent of an alkaline earth metal or of zinc or ammonium, then treating this dispersion or solution with an alkali metal, and, if x is >1, after the end of the development of $H_2$ with the necessary amount of sulfur, and directly subsequently further reacting with a compound of the formula $$\text{Z—Alk—Hal} \quad (3)$$

wherein Hal is a chlorine or bromine atom, separating the organic product from the halide formed and removing the organic solvent.

2. A process according to claim 1 wherein Z is

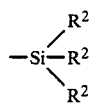

and each $R^2$ is alkoxy of 1–5 carbon atoms.

3. A process according to claim 1 wherein as solvent there is used the alcohol or aromatic hydroxyl compound having the group $R^2$.

4. A process according to claim 3 wherein the alkali metal is sodium or potassium.

5. A process according to claim 1 wherein the alkali metal is sodium or potassium.

6. A process according to claim 4 wherein Z is

and each $R^2$ is alkoxy of 1–5 carbon atoms.

7. A process according to claim 1 wherein the solvent is an alcohol.

* * * * *